(12) United States Patent
Hamdouchi

(10) Patent No.: US 8,431,706 B2
(45) Date of Patent: Apr. 30, 2013

(54) 1,2,3,4-TETRAHYDROQINOLINE DERIVATIVE USEFUL FOR THE TREATMENT OF DIABETES

(75) Inventor: Chafiq Hamdouchi, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/570,342

(22) Filed: Aug. 9, 2012

(65) Prior Publication Data

US 2013/0045990 A1 Feb. 21, 2013

Related U.S. Application Data

(60) Provisional application No. 61/524,462, filed on Aug. 17, 2011.

(51) Int. Cl.
*A61K 31/47* (2006.01)
*C07D 215/00* (2006.01)
(52) U.S. Cl.
USPC .......................................... 546/153; 514/312
(58) Field of Classification Search .................. 546/153; 514/312
See application file for complete search history.

(56) References Cited

U.S. PATENT DOCUMENTS

2006/0004012 A1 1/2006 Akerman et al.

FOREIGN PATENT DOCUMENTS

WO 2011066183 A1 6/2011

*Primary Examiner* — John Mabry
(74) *Attorney, Agent, or Firm* — MaCharri Vorndran-Jones; James B. Myers

(57) ABSTRACT

The present invention provides a compound of the formula below

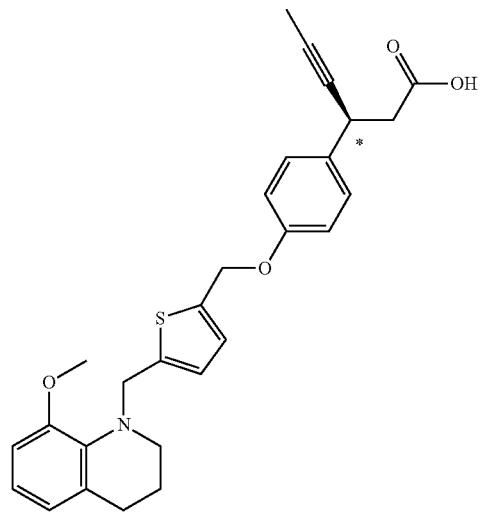

or a pharmaceutical salt thereof, methods of treating diabetes using the compound and a process for preparing the compound.

5 Claims, No Drawings

1,2,3,4-TETRAHYDROQINOLINE DERIVATIVE USEFUL FOR THE TREATMENT OF DIABETES

Diabetes is a serious health care problem facing the developing world. It would be desirable to provide a safe and effective oral treatment for diabetes. Some successful commercially available oral treatments for type two diabetes (T2D) are believed to act through modulation of the peroxisome proliferator-activated receptor (PPAR) gamma receptor. Administration of these medicines has been associated with undesired adverse effects that sometimes include hypoglycemia, liver damage, gastrointestinal disease, weight gain, or other undesired effects that may be associated with the PPAR gamma activity. New treatment options offering a more desirable safety profile for managing T2D are desired to effectively treat or prevent diabetes in more patients. In particular, novel mechanism-based treatment methods that may minimize or avoid effects that have been associated with PPAR gamma activation are especially desired.

The G protein-coupled receptor 40 (GPR-40), also known as Free Fatty Acid Receptor 1 (FFA1 or FFAR1), is reported as predominately expressed at high levels in rodent pancreatic beta cells, insulinoma cell lines, and human islets. This receptor is activated by medium and long-chain fatty acids. The glucose dependency of insulin secretion is an important feature of activating GPR-40, making this receptor an excellent target for developing efficacious therapies with a desired safety profile for use in the treatment of T2D. Compounds that offer efficacy and a more desirable safety profile compared to existing therapies such as insulin and sulfonylureas can be especially desirable.

Two recently published patent applications, US20110092531 and WO2011066183 disclose compounds possessing a spiro-bicyclic group which exhibit GPR-40 activity.

This invention provides a compound for the treatment of diabetes particularly T2D. The compound for this invention is a potent activator of GPR-40. This invention provides a desired novel treatment option acting through a pharmacological mechanism that is unique compared to commercially available treatments and further provides a compound that selectively activates GPR-40 as compared to PPAR gamma. The pharmacological profile of the compound of this invention, as a selective GPR-40 activator, can be particularly desirable for use in the treatment of T2D. Additionally, the selective GPR-40 modulation may provide a particularly desirable safety profile for use in the treatment of T2D by avoiding effects associated with PPAR gamma modulation.

The present invention provides a compound of the Formula I below:

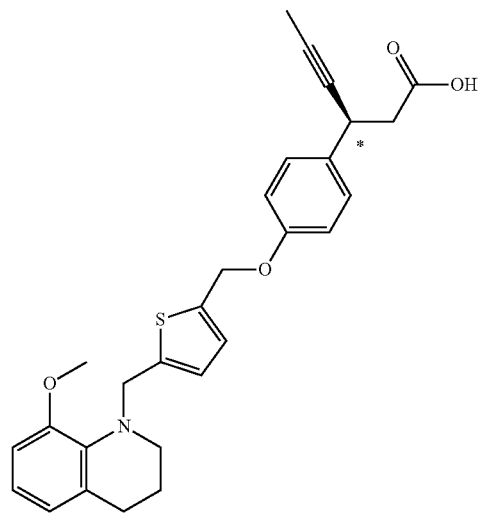 [SMILES: CC#C[C@@H](CC(=O)O)c1ccc(OCc2ccc(CN3CCCc4cccc(OC)c43)s2)cc1]

or a pharmaceutically acceptable salt thereof.

The compound of the present invention can have a chiral carbon identified in the structure above with an asterisk (*). The preferred compound has the configuration shown above, which by convention is known as the S configuration.

The present invention also provides a pharmaceutical composition comprising a compound of Formula I as described above or a pharmaceutically acceptable salt thereof together with one or more pharmaceutically acceptable carriers, diluents or excipients.

The present invention also provides a pharmaceutical composition comprising a compound of Formula I as described above or a pharmaceutically acceptable salt thereof together with one or more pharmaceutically acceptable carriers, diluents or excipients, and optionally one or more therapeutic agents.

The present invention also provides a method for treating diabetes in a mammal The method comprises administering to the mammal in need of treatment a compound as described above for Formula I, or a pharmaceutically acceptable salt thereof. More preferably the present invention provides a method of treating type two diabetes in a mammal in need of treatment by administering to the mammal a compound as described above for Formula I or a pharmaceutically acceptable salt thereof. Preferably the mammal is a human.

The present invention also provides a method for treating diabetes in a mammal by administering to the mammal in need of treatment a pharmaceutical composition comprising a compound as described above for Formula I, or a pharmaceutically acceptable salt thereof. More preferably the present invention provides a method of treating type two diabetes in a mammal in need of treatment by administering to the mammal a pharmaceutical composition comprising a compound as described above for Formula I, or a pharmaceutically acceptable salt thereof. Preferably the mammal is a human.

The present invention provides a compound according to Formula I or a pharmaceutically acceptable salt thereof as described above for use in therapy.

In yet another form, the present invention provides a compound as described above according to Formula I, a pharmaceutically acceptable salt thereof, or pharmaceutical composition for use in the treatment of diabetes in a mammal in need thereof. Preferably the use is for the treatment of type two diabetes and the mammal is a human.

The present invention provides use of a compound according to Formula I, or a pharmaceutically acceptable salt thereof, in the manufacture of a medicament for the treatment of diabetes. Preferably the medicament is for the treatment of type two diabetes and for treating mammal particularly humans.

In yet another form, the present invention provides an intermediate compound of the Formula II

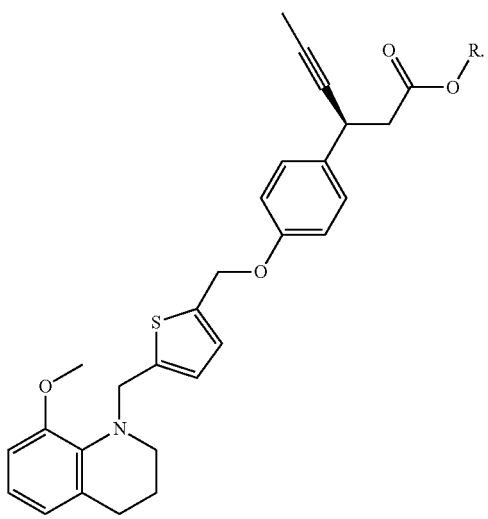

II wherein R is selected from a $C_{1-4}$ alkyl, $C_{1-4}$ haloalkyl, $C_{3-6}$ cycloalkyl, $C_{1-4}$ alkyl-$C_{3-6}$ cycloalkyl, phenyl, and $C_{1-5}$ alkylphenyl to provide a compound of Formula I, or a pharmaceutically acceptable salt thereof. Preferred R groups include $C_{1-2}$ alkyl, $C_{1-2}$ haloalkyl, phenyl, and $C_{1-2}$ alkylphenyl. Particularly preferred R groups include methyl, ethyl, phenyl, and benzyl.

The present invention also provides a process of preparing (3S)-3-[4-[[5-[(8-Methoxy-3,4-dihydro-2H-quinolin-1-yl) methyl]-2-thienyl]methoxy]phenyl]hex-4-ynoic acid described above for Formula I. The method comprises deprotecting or de-esterifying the intermediate compound according to Formula II to prepare the compound of Formula 1 or a pharmaceutically acceptable salt thereof.

One skilled in the art would readily understand and be able to implement deprotecting reactions without undue experimentation. It will be recognized by those skilled in the art that in addition to the carboxylic acid and protected carboxylic acid, other functional groups that can be readily converted to a carboxylic acid can be used in place the carboxylic acid or protected acid. Such functional groups, preparations, and transformations of these groups to carboxylic acids can be found in "Comprehensive Organic Transformations: A Guide to Functional Group Preparations" by Larock. R. C, Wiley VCH, 1999 and in "March's Advanced Organic Chemistry, Reactions, Mechanisms and Structure" Smith, M. B., and March, J., Wiley-Interscience, 6th Ed. 2007.

The compound of the present invention, (3S)-3-[4-[[5-[(8-Methoxy-3,4-dihydro-2H-quinolin-1-yl)methyl]-2-thienyl] methoxy]phenyl]hex-4-ynoic acid, can be provided as a pharmaceutically acceptable salt. "Pharmaceutically-acceptable salt" refers to salts of the compound of the invention considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

The term "pharmaceutically acceptable carrier, diluent, or excipients" means that the carrier, diluent, and excipients are pharmaceutically compatible with the other ingredients of the composition.

Certain substituents have been eliminated in the following Schemes for the sake of clarity and is not intended to limit the teaching of the Schemes in any way. Furthermore, individual isomers, enantiomers, or diastereomers may be separated at any convenient point in the synthesis of the compound of Formula I by methods such as chiral chromatography. Additionally, the intermediates described in the following Schemes and preparations contain a number of nitrogen, hydroxy, and acid protecting groups such as esters. The variable protecting group may be the same or different in each occurrence depending on the particular reaction conditions and the particular transformations to be performed. The protection and deprotection conditions are well known to the skilled artisan and are described in the literature. See. e.g., Greene and Wuts, *Protective Groups in Organic Synthesis*, (T. Greene and P. Wuts, eds., 2d ed. 1991).

The abbreviations used herein are defined according to *Aldrichimica Acta*, Vol. 17, No. 1, 1984. Other abbreviations are defined as follows: "ADDP" refers to 1-(azodicarbonyl) dipiperidine; "BSA" refers to Bovine Serum Albumin; "DIBAL-H" refers to diisobutylaluminum hydride; "DIPEA" refers to diisopropylethyl amine; "DMEM" refers to Dulbecco's Modified Eagle's Medium; "DTT" refers to dithiothreitol; "ESI" refers to electrospray ionization "EtOAc" refers to ethyl acetate; "EtOH" refers to ethyl alcohol or ethanol; "F12" refers to Ham's F12 medium; "FBS" refers to Fetal Bovine Serum; "HEK" refers to human embryonic kidney; "$IC_{50}$" refers to the concentration of an agent that produces 50% of the maximal inhibitory response possible for that agent; "MeOH" refers to methyl alcohol or methanol; "NBS" refers to N-bromosuccinimide; "PPAR" refers to peroxisome proliferator-activated receptor; "PPRE" refers to peroxisome proliferator response element; "RFU" refers to relative fluorescence unit; "RPMI" refers to Roswell Park Memorial Institute; "RT" refers to ambient room temperature; "THF" refers to tetrahydrofuran; and "TK" refers to thymidine kinase.

The term alkyl as used herein is a straight chain alkyl such as ethyl or n-propyl, or a branched chain alkyl such as isopropyl or tert-butyl. The term $C_{1-4}$ haloalkyl refers to an alkyl group that has 1, 2, 3, or more halo groups attached to the carbons of the alkyl chain. If there are two or more halogens, the halogens need not be attached to the same carbon. This term also includes perhalo alkyls where all the hydrogen atoms of the alkyl group are replaced with a halogen.

In the schemes below, all substituents unless otherwise indicated, are as previously defined. The reagents and starting materials are generally readily available to one of ordinary skill in the art. Others may be made by standard techniques of organic and heterocyclic chemistry, which are analogous to the syntheses of known structurally-similar compounds, and the following procedures described in the Preparations and Examples including any novel procedures.

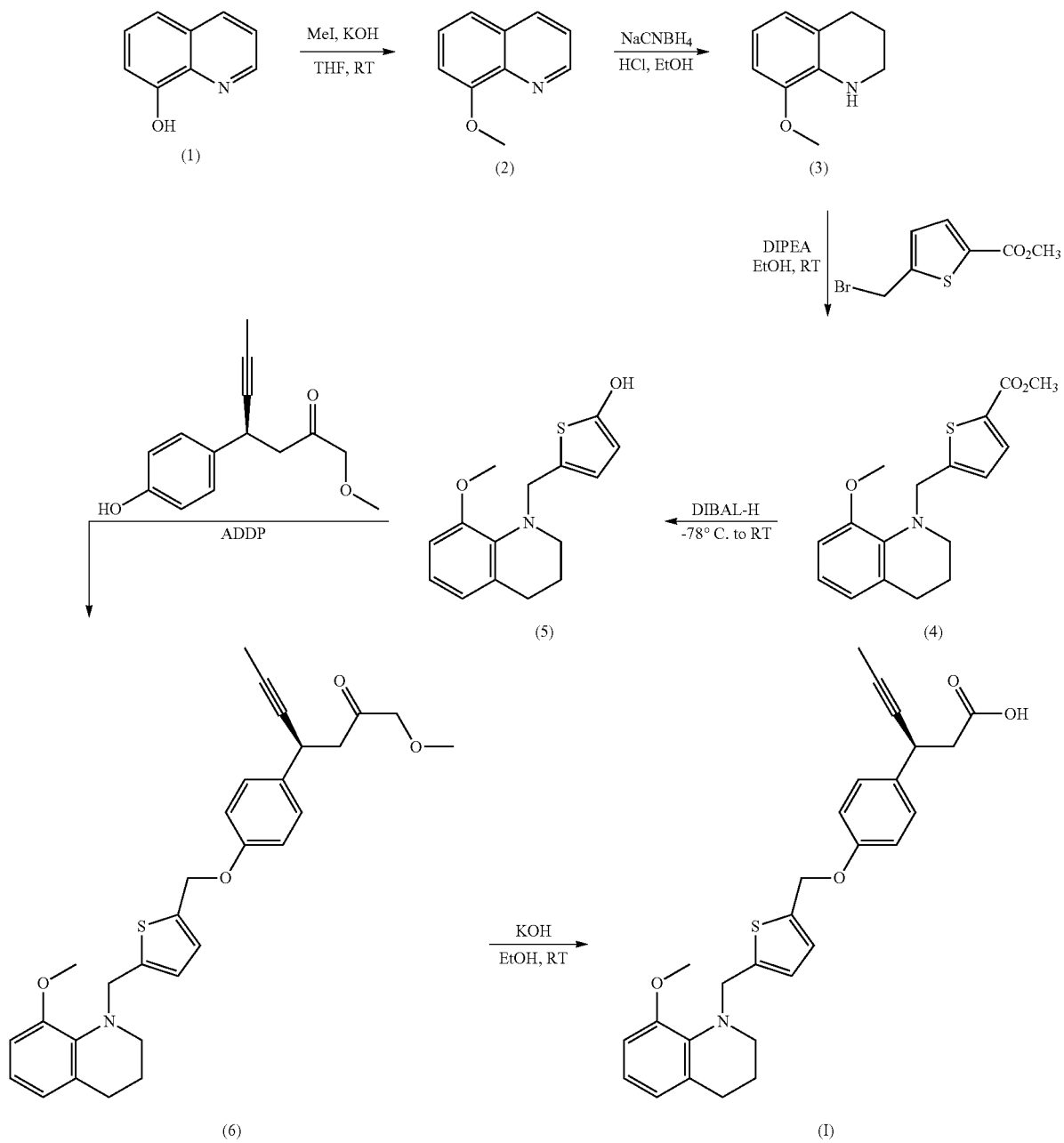

Scheme 1

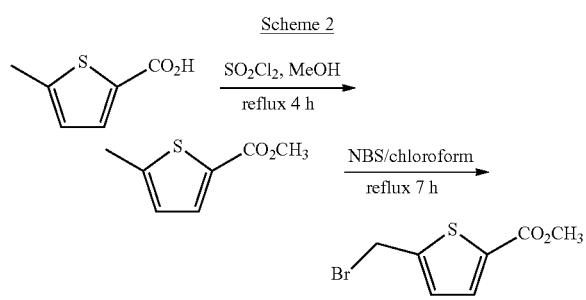

Scheme 2

PREPARATIONS AND EXAMPLES

The following Preparations and Examples further illustrate the invention and represent typical synthesis of the compound of Formula (I). The compounds are named by IUPACNAME ACDLABS or Symyx Draw 3.2.

Preparation 1

8-Methoxyquinoline

Add potassium hydroxide (435 g, 7.76 mol) to a solution of 8-hydroxy quinoline (250 g, 1.724 mol) in THF (10 L) at ambient temperature and stir. Add methyl iodide (435 g, 2.58 mol) dropwise and stir overnight. Filter the reaction mixture and wash the solid with THF (2 L). Concentrate the solution to dryness; add water; extract with dichloromethane (2×3 L); combine the organic layers; and wash with brine. Collect the organic layers and dry over sodium sulfate. Remove the solids by filtration. Collect the filtrate and concentrate under reduced pressure to give a red oil, which solidifies on standing, to give the title compound (281 g, 102%), which can be used without further purification. ESI (m/z) 160(M+H).

Preparation 2

8-Methoxy-1,2,3,4-tetrahydroquinoline

Add sodium cyanoborohydride (505 g, 8.11 mol) in EtOH (1 L) to a solution of 8-methoxy quinoline (425 g, 2.673 mol) in EtOH (9 L), and stir. Cool the reaction mixture to an internal temperature of 0° C. and add HCl (35%, 1.12 L, 10.962 mol) dropwise over 60 min so that the internal temperature did not rise above 20° C. Allow the reaction mixture to warm to ambient temperature and then heat to reflux for 2.5 hours. Cool to ambient temperature and stir overnight. Add ammonium hydroxide (25%, 1 L); dilute with water (15 L); and extract the mixture with dichloromethane (3×10 L). Combine the organic layers and dry over sodium sulfate. Remove the solids by filtration. Collect the filtrate and concentrate under reduced pressure to give a residue. Purify the residue by silica gel flash chromatography, eluting with ethyl acetate: hexane (1:10) to give the title compound (357 g, 82%). ESI (m/z) 164(M+H).

Preparation 3

Methyl-5-methylthiophene-2-carboxylate

Add thionyl chloride (153 ml, 2.1 mol) dropwise over 20 min to a solution of 5-methylthiophene-2-carboxylic acid (100 g, 0.703 mol) in MeOH (1 L) at 0° C. and stir. After the addition is complete, heat the reaction mixture to reflux for 3.5 hours. Cool and concentrate in vacuo to give a thick oil. Dilute the oil with EtOAc (500 ml) and sequentially wash with water (300 ml) then brine (300 ml). Dry the organic layer over sodium sulfate. Remove the solids by filtration. Collect the filtrate and concentrate under reduced pressure to give the title compound (106 g, 97%), which is used without further purification. ESI (m/z) 156(M+H).

Preparation 4

Methyl 5-(bromomethyl)thiophene-2-carboxylate

Add freshly recrystallised NBS (323.8 g, 1.81 mol) to a solution of methyl-5-methylthiophene-2-carboxylate (258 g, 1.65 mol) in chloroform (2.6 L) at room temperature, and stir. Add benzoyl peroxide (3.99 g, 0.016 mol) and heat the reaction mixture to reflux for 7 hours. Cool the reaction mixture to ambient temperature and filter through diatomaceous earth. Wash the filter cake with chloroform (250 ml). Collect the organic layers and remove the solvent to give the title compound (388 g, 100%), which is used without further purification. ESI (m/z) 236(M+H).

Preparation 5

Methyl-5-[8-methoxy-3,4-dihydro-2H-quinolin-1-yl) methyl]thiophene-2-carboxylate Add methyl-5-(bromoethyl)thiophene-2-carboxylate (432.5 g, 1.84 mol) in EtOH (500 ml) to a solution of 8-methoxy-1,2,3,4-tetrahydroquinoline (300 g 1.84 mol) in EtOH (1 L) and stir. Add DIPEA (641 ml, 3.67 mol) dropwise and stir at room temperature overnight. After completion of the reaction, remove the EtOH in vacuo, and add water (5 L). Extract the aqueous with EtOAc (3×3 L); combine the organic layers; and dry over sodium sulfate. Filter the solution and concentrate under reduced pressure to give a residue. Purify the residue by silica gel flash chromatography eluting with ethyl acetate: hexane (6:94) to give the title compound (325 g, 56%). ESI (m/z) 318(M+H).

Preparation 6

[5-[(8-Methoxy-3,4-dihydro-2H-quinolin-1-yl)methyl]-2-thienyl]methanol

Add DIBAL-H (1 M in toluene 2.7 L, 2.66 mol) slowly via a cannula over a period of 1.5 h to a stirred solution of methyl-5-(8-methoxy-3,4-dihydroquinolin-1(2H)-yl)methyl)thiophene-2-carboxylate (281 g, 0.886 mol) in THF (4 L) at −70° C. Monitor the reaction via thin layer chromatography (TLC) for completion. After completion of the reaction, allow the reaction mixture to warm to 20° C. and add a saturated solution of ammonium chloride. Add a solution of sodium potassium tartrate (1.3 Kg in 5 L of water), and stir overnight. Separate the organic layer; extract the aqueous phase with EtOAc (2×5 L); then combine the organic layers; and dry the combined organic layers over sodium sulfate. Remove the solids by filtration. Remove the solvent from the filtrate under reduced pressure to give the title compound as a white solid (252 g, 98%). ESI (m/z) 290(M+H).

Preparation 7

Ethyl(3S)-3-[4-[[5-[(8-methoxy-3,4-dihydro-2H-quinolin-1-yl)methyl]-2-thienyl]methoxy]phenyl] hex-4-ynoate Add tributylphosphine (50% solution in EtOAc, 543 ml, 1.34 mol) to a solution of ADDP (282.5 g, 1.5 eq) in THF (3 L) and cool the mixture to an internal temperature of 0° C., then stir for 15 minutes. Add (S)-ethyl 3-(4-hydroxyphenyl) hex-4-ynoate (173.5 g, 0.747 mol) in THF (3 L) dropwise over 15 min; then add 5-((8-methoxy-3,4-dihydroquinolin-1 (2H)-yl)methyl)thiophene-2-yl)methanol (216 g, 0747 mol) in THF (5 L) dropwise. Allow the reaction mixture to warm to ambient temperature and stir overnight. Filter the reaction mixture through diatomaceous earth and wash the filter cake with ethyl acetate (2 L). Concentrate the organic filtrate to dryness. Add water (4 L); extract with ethyl acetate (3×5 L); combine the organic layers; and dry the combined organic layers over sodium sulfate. Remove the solids by filtration and concentrate under reduced pressure to give an oil. Purify the residue by silica gel flash chromatography by eluting with ethyl acetate: hexane (6:94) to give the title compound (167 g, 44%). ESI (m/z) 504(M+H).

Example 1

(3S)-3-[4-[[5-[(8-Methoxy-3,4-dihydro-2H-quinolin-1-yl)methyl]-2-thienyl]methoxy]phenyl]hex-4-ynoic acid

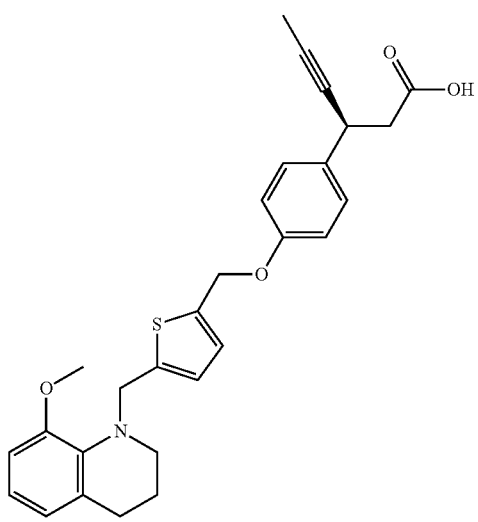 [SMILES: CC#C[C@@H](CC(=O)O)c1ccc(OCc2ccc(CN3CCCc4cccc(OC)c43)s2)cc1]

Add a solution of potassium hydroxide (49.76 g, 0.88 mol) in water (372 ml) to a solution of (S)-ethyl-3-(4-((5-8-methoxy-3,4-dihydroquinolin-1(2H)-yl)methyl)thiophen-2-yl) methoxy)phenyl)hex-4-ynoate (149 g, 0.296 mol) in EtOH (1.49 L) at room temperature and stir overnight. Concentrate the reaction mixture to dryness and add water (1.3 L). Extract the resulting solution with EtOAc (2×300 ml) and separate. Adjust the pH of the aqueous layer to pH=6 with 2 N HCl. Collect the resulting solids. Recrystallise the solids from hot MeOH (298 ml, 2 vol) to give the title compound (91 g, 65%). ESI (m/z) 476(M+H).

GPR40: Information

Results of studies using transgenic mice over-expressing the human GPR40 gene under control of the insulin II promoter recently reported by Nagasumi further support that GPR40 plays an important role in the regulation of GDIS and plasma glucose levels in-vivo, especially in rodent models of insulin resistance. Nagasumi K, et. al., *Overexpression of GPR40 in pancreatic β-cells augments glucose-stimulated insulin secretion and improves glucose tolerance in normal and diabetic mice*, Diabetes 58: 1067-1076, 2009. See also, Briscoe C P et al., *The orphan G protein-coupled receptor GPR40 is activated by medium and long chain fatty acids*, Journal Biological Chemistry 278: 11303-11311, 2003. These findings further support that the development of new GPR40 modulator compounds may be particularly desired for use in the treatment of T2D.

Calcium Flux Primary Assay

The compound of Example 1 is tested essentially as described below and exhibits an $EC_{50}$ value for the Calcium Flux Primary assay of lower than 1 μM.

This assay is used to screen compounds by measuring the increase in intracellular calcium levels that results when a ligand binds and activates GPR40, thus demonstrating the potency and efficacy of GPR40 agonists. HEK293 cells over expressing the human GPR40 cDNA maintained in Dulbecco's modified Eagle's medium with F12 medium in 3:1 ratio supplemented with 10% FBS and 800 μg/ml geneticin at 37° C. and 5% $CO_2$ are employed for the study. Agonist assays are performed using a Calcium 4 Dye assay kit (Molecular Devices) in the presence of 0.1% fatty acid free BSA in the assay buffer (1× HBSS (Hank's Balanced Salt Solution) & 20 mM HEPES (4-(2-hydroxyethyl)-1-piperazineethanesulfonic acid). Receptor activation is measured as an increase in intracellular calcium using the Fluorometric Imaging Plate Reader (FLIPR). Maximum change in fluorescence over the base line is used to determine agonist response. An $EC_{50}$ (effective concentration at half the maximal response) value of the compound is calculated using Excel Fit software (version 4; IDBS) by plotting concentration vs relative fluorescence units (RFUs). Percent efficacy is calculated based on the maximal response exhibited by compound compared to the natural ligand, linoleic acid. The test compound of Example 1 has an $EC_{50}$ of 152+/−52 nM with 84+/−24% efficacy when examined in this assay. These results further demonstrate the desired potency and efficacy of this compound as a GPR40 agonist.

Glucose Dependent Insulin Secretion (GDIS) Assays

Because activation of GPR40 is known to result in insulin secretion, which is dependent on high glucose concentrations, two separate assay systems (an insulinoma cell line and primary rodent islets) are developed to further characterize compounds that are known to increase intracellular calcium in the GPR40 primary assay discussed above.

GDIS assays are performed using the mouse insulinoma cell line Min6. The Min6 cells are maintained in Dulbecco's Modified Eagle's Medium (DMEM) containing non-essential amino acids, 10% FBS, 50 mM 2-mercaptoethanol and 1% penicillin and streptomycin at 37° C. plus 5% $CO_2$. On the day of the experiment, the cells are washed twice with 200 μl of pre-warmed Krebs-ringer buffer without glucose. Addition of 200 μL of pre-warmed Krebs-ringer buffer containing 2.5 mM glucose is used to starve the cells followed by the addition of compounds in the presence of a high concentration of glucose (25 mM). The plate is incubated at 37° C. for 2 hours. At the end of the 2 h incubation, the supernatant is gently transferred into a Millipore filter plate and spun at 200 g (gravitational force) for 3 minutes. Insulin is assayed using a Mercodia Insulin estimation kit. Addition of Example 1 at 0.01, 0.1, 1.0, and 10.0 μM plus 25 mM glucose to the Min6 cells resulted in a dose dependent increase in insulin secretion with a statistically significant (P<0.01) increase (2.68 fold over that achieved with 25 mM glucose) at the 1.0 μM dose.

GDIS assays using primary rodent pancreatic islets of Langerhans are also used to characterize the exemplified compound. Pancreatic islets are isolated from male SD (Sprague Dawley) rats by collagenase digestion and Histopaque density gradient separation. The islets are cultured overnight in RPMI-1640 medium with GlutaMAXn (stabilized, dipeptide form of L-glutamine (Invitrogen catalog #61870-010)) to facilitate recovery from the isolation process. Insulin secretion is determined by a 90 minute incubation in EBSS (Earle's Balances Salt Solution) buffer in a 48-well plate. Briefly, islets are first preincubated in EBSS with 2.8 mM glucose for 30 min, and are then transferred to a 48-well plate (four islets/well) containing 150 μl 2.8 mM glucose, and incubated with 150 μl of EBSS with 2.8 or 11.2 mM glucose in the presence or absence of test compound for 90 minutes. The buffer is removed from the wells at the end of the incubation, and assayed for insulin levels using the Rat Insulin ELISA kit (Mercodia). In this assay system, incubation of Example 1 at 1, 3, and 10 μM with rat islets and 11.2 mM glucose results in a statistically significant (P<0.05) increase in insulin at 3.0 uM (2.1-fold) compared to that achieved with 11.2 mM glucose. Thus, the compound of Example 1 induces insulin production under the conditions of this assay.

Selectivity Assays:

Peroxisome Proliferator-Activated Receptor (PPAR) α, δ, and γ Binding and Functional Assays:

Because GPR40 is known to be activated by ligands to PPARγ, the exemplified compound is examined in PPARα, PPARδ, and PPARγ binding and functional assays to determine the selectivity of the compound of Example 1 for GPR40. The compound of Example 1 is tested essentially as described below for PPAR binding and it exhibits binding values greater than 1000 nM with 10 μM concentrations of test compound, and is thus considered negative for PPAR activity.

Binding affinities of the compound for the PPAR α, δ, and γ receptors are assessed using Scintillation Proximity Assay (SPA) technology. Biotinylated oligonucleotide Direct Repeat 2 (DR2) is used for binding the receptors to Yttrium silicate streptavidin-coated SPA beads. PPAR α, δ, γ and retinoid X receptor (RXR) α are over expressed in HEK293 cells, and cell lysates containing the specific receptors are used in the individual assays. The DR2 is attached to the SPA beads over a 30 minute period in a binding buffer containing 10 mM HEPES pH 7.8, 80 mM KCl, 0.5 mM $MgCl_2$, 1 mM DTT, 0.5% 3[(3-cholamidopropyl)dimethylammonio]-propanesulfonic acid (CHAPS), and 4.4% bovine serum. The cell lysates are incubated in each well with one of 11 concentrations of compound in the presence of a radio-labeled (~0.033.8 μCi $^3H$) PPAR α/δ dual agonist reference compound (butanoic acid, 2-[4-[2-[[[(2,4-difluorophenyl)amino] carbonyl]heptylamino]ethyl]phenoxy]-2-methyl, see Burris T. P. et al., *Molecular Pharmacology* 2005, 67, (3) 948-954)—for the alpha and delta receptor assays and a radio-labeled (~0.037.3 μCi$^3H$) PPARγ agonist reference compound (propanoic acid, 2-methyl-2-[4-[3-[propyl[[5-(2-pyridinyl)-2-thienyl]sulfonyl]amino]propyl]phenoxy], see Burris T. P. et al., *Molecular Pharmacology* 2005, 67, (3) 948-954) for the gamma receptor assays, 110.3 μg of Yttrium SPA Streptavidin coated beads, 0.126 nM HD Oligo DR2, and either 0.3 μg PPARα with 0.5 μg RXRα, 0.5 μg PPARδ with 0.5 μg RXRα, or 1.25 μg PPARγ with 3.03 μg RXRα in the binding buffer above plus 14% glycerol and 5 μg of sheared salmon sperm DNA. Non-specific binding is determined in the presence of 10,000 nM of the unlabeled PPAR α/δ dual agonist reference compound for the alpha and delta receptor assays and the PPARγ agonist reference compound for the gamma receptor assay. The binding reaction (100 μl per well in a 96 well [Costar 3632] plate) is incubated for 10 h and counted disintegration per minutes (dpm) on a Wallac Microbeta. Receptor binding affinity ($IC_{50}$) for the compound is determined by fitting an 11 point concentration-response curve with a 4-parameter logistic equation. $K_i$ is determined from the $IC_{50}$ using the Cheng-Prussoff equation and Kd determined by saturation binding. For the compound of Example 1, no binding is detected in any of the three PPAR binding assays with concentrations up to 10 μM. Thus, the assays set forth herein support that the compound of Example 1 selectively activates GPR40 while avoiding the undesired PPAR activity. The relative $IC_{50s}$ for the exemplified compound when tested up to 30 μM is greater than 10 μM for the PPAR isoforms, supporting that the exemplified compound avoids PPAR activity while providing the desired GPR40 activation.

Gal4 PPARα, Gal4 PPARδ, and PPARγ reporter functional assays are also used to monitor the selectivity of the exemplified compound. CV1 cells, which are derived from the renal tissue of an African green monkey, are transfected with various receptor and reporter plasmids using Fugene. For the Gal4 PPARα and PPARδ assays, a reporter plasmid containing five tandem copies of the yeast transcription protein Gal4 response element, cloned upstream of a firefly luciferase gene driven by the major late promoter of adenovirus, is transfected together with a Simian Virus 40 (SV40) driven plasmid constitutively expressing a hybrid protein containing the Gal4 DNA binding domain (DBD), and either the PPARα or PPARδ ligand binding. For the PPARγ assay, plasmids encoding PPARγ and RXRα, both driven by a cytomegalovirus (CMV) promoter are transfected together with a plasmid containing luciferase reporter cDNA driven by the TK promoter and a receptor response element (2×PPRE). Cells are transfected in T225 $cm^2$ cell culture flasks in DMEM media with 5% charcoal-stripped FBS. After an overnight incubation, transfected cells are trypsinized; plated in opaque 96 well dishes (15,000 cells/well) in DMEM media containing 5% charcoal-stripped FBS, incubated for 4 h; and exposed to 0.17 ηM to 10 μM of test compound or reference compound in half log dilutions. After 24 hours incubation with the compound, cells are lysed and luciferase activity is determined as a measure of receptor activation by luminescence. Data are fitted to a four parameter-fit logistics model to determine $EC_{50}$ values. The maximum percent stimulation is determined versus maximum stimulation obtained with 10 μM of an appropriate PPAR agonist reference compound. No functional activation of PPARα, PPARδ, or PPARγ is detected with the compound of Example 1 when examined up to 10 μM in the specific PPAR co-transfection (CTF)/functional assays described above. Thus, the assay supports that the exemplified compound avoids PPAR agonist activity, as desired.

In Vivo Efficacy: Intraperitoneal Glucose Tolerance Test (IP-GTT)

To examine the ability of exemplified the compound to activate GPR40 in-vivo resulting in anti-diabetic efficacy, i.e. reduction in plasma glucose levels, a 4-day intraperitoneal glucose tolerance test (ipGTT) study is completed, and the data is shown for the compound tested below.

Male Balb/c (Albino mice) mice (8-9 weeks of age) are single housed, and fed with normal rodent chow diet and water ad libitum. Animals are weighed; randomized by body weight; and their daily body weights are recorded Animals are dosed once per day orally for three days using a formulation carrying methylcellulose and tween-80. On the night before Day 4, animals are fasted overnight. On the morning of Day 4, animals are dosed orally with compound or vehicle alone 60 minutes prior to the glucose tolerance test (glucose 2 g/kg, i.p.). Blood glucose levels are determined from tail bleeds taken at 0, 3, 7, 15, 30, and 60 min after glucose challenge. The blood glucose excursion profile from t=0 to t=60 min is used to integrate an area under the curve (AUC) for each treatment. Percent lowering in glucose is calculated from the AUC data of the compound with respect to the AUC of vehicle group. The test compound is orally administered at 0.3, 1.0, 3.0, 10, or 30 mg/kg, and a positive control (3-[4-(2-methyl-benzyloxy)-phenyl]-hex-4-ynoic acid, see WO2005086661.) is administered at 10 mg/kg. Glucose levels are significantly lowered compared to those achieved with the vehicle control at the 15 minute time points with the 3, 10 and 30 mg/kg doses and at the 30 and 60 minute time points with the 1.0, 3.0, 10, and 30 mg/kg doses of Example 1. Glucose levels are lowered at the 15, 30, and 60 minute time points for the positive control. The $ED_{50}$ for this compound based on AUCs for glucose lowering is 1.0 mg/kg. Results from this study demonstrate that activation of GPR40 by Examples 1 leads to in-vivo anti-diabetic efficacy.

The exemplified compound of the present invention can be readily formulated into pharmaceutical compositions in accordance with accepted practices known in the art such as found in Remington's "Pharmaceutical Sciences", Gennaro, Ed., Mack Publishing Co. Easton, Pa. 1990 such as tablets, solid or gel filled capsules, powders, suspensions, or solutions. The composition can also include one or more pharmaceutically acceptable carriers, excipients, and diluents. Non limiting examples of pharmaceutically acceptable carriers, excipients, and diluents are suitable for such formulations include the following: starch, sugars, mannitol, and silica derivatives; binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium, and magnesium stearate, and solid polyethyl glycols.

Preferred pharmaceutical compositions include formulated as a tablet or capsule for oral administration. The tablet or capsule can include a compound of the present invention in an amount effective to treat diabetes particularly type two diabetes.

The pharmaceutical composition is administered to a patient in amounts effective to treat diabetes, more particularly, type two diabetes. An appropriate amount or dose effective to treat a patient can be determined by a health care provider.

What is claimed is:

1. A compound which is:

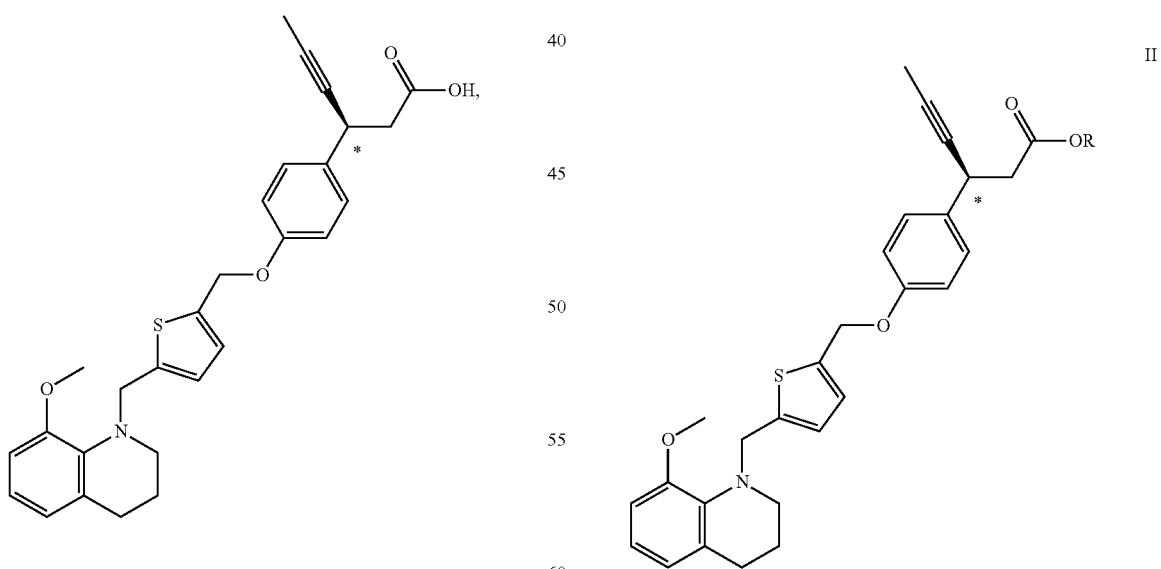

or a pharmaceutically acceptable salt thereof.

2. A pharmaceutical composition comprising a compound according to claim 1 or a pharmaceutically acceptable salt thereof and at least one of a pharmaceutically acceptable carrier, diluent, or excipient.

3. A pharmaceutical composition according to claim 2 further comprising one or more additional therapeutic agents.

4. A compound according to formula II

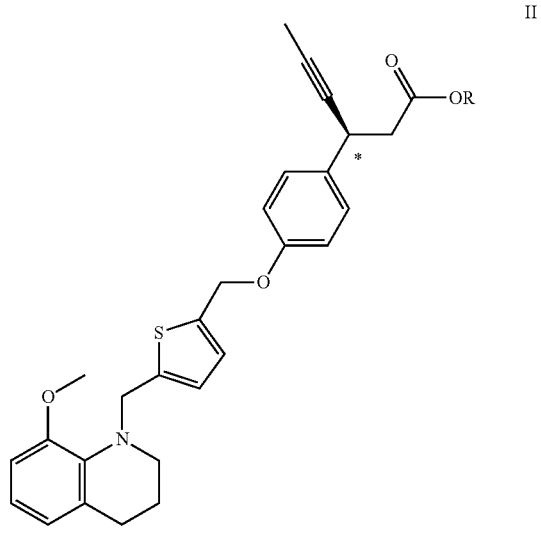

wherein R is selected from: $C_{1-4}$ alkyl, $C_{1-4}$ haloalkyl, $C_{3-6}$ cycloalkyl, $C_{1-4}$ alkyl-$C_{3-6}$ cycloalkyl, phenyl, and $C_{1-5}$ alkylphenyl.

5. A method of preparing (3S)-3-[4-[[5-[(8-Methoxy-3,4-dihydro-2H-quinolin-1-yl)methyl]-2-thienyl]methoxy]phenyl]hex-4-ynoic acid or a pharmaceutically acceptable salt thereof, said method comprising de-esterifying a compound of formula II;

Where R is selected from: $C_{1-4}$ alkyl, $C_{1-4}$ haloalkyl, $C_{3-6}$ cycloalkyl, $C_{1-4}$ alkyl-$C_{3-6}$ cycloalkyl, phenyl, and $C_{1-5}$ alkylphenyl to provide a compound of formula I, or a pharmaceutically acceptable salt thereof

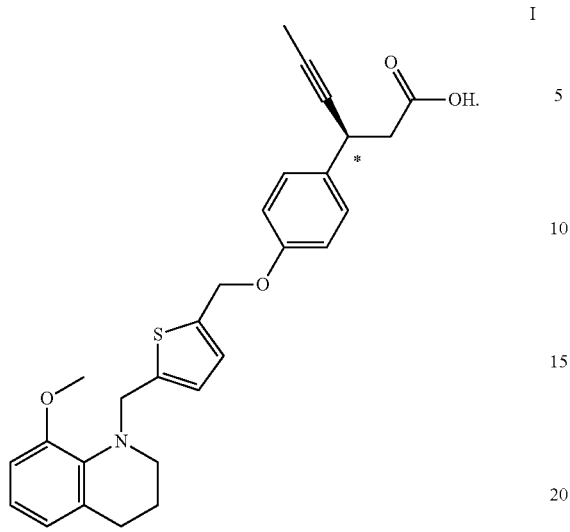
* * * * *

UNITED STATES PATENT AND TRADEMARK OFFICE
CERTIFICATE OF CORRECTION

PATENT NO. : 8,431,706 B2
APPLICATION NO. : 13/570342
DATED : April 30, 2013
INVENTOR(S) : Chafiq Hamdouchi It is certified that error appears in the above-identified patent and that said Letters Patent is hereby corrected as shown below:

On the Title page, Item (54) and in the Specification, column 1, line 1, Title please delete "TETRAHYDROQINOLINE" and insert --TETRAHYDROQUINOLINE--, therefor.

Signed and Sealed this
Sixteenth Day of July, 2013

Teresa Stanek Rea
*Acting Director of the United States Patent and Trademark Office*